(12) United States Patent
Grune

(10) Patent No.: US 9,782,610 B2
(45) Date of Patent: *Oct. 10, 2017

(54) NONTOXIC, NON-ENDOCRINE DISRUPTING, CYTOPROTECTIVE, UV-RADIATION RESISTANT SUNBLOCK COMPOSITIONS

(75) Inventor: Guery L. Grune, Virginia Beach, VA (US)

(73) Assignee: 3rd Rock Sunblock, Inc., Virginia Beach, VA (US)

( * ) Notice: Subject to any disclaimer, the term of this patent is extended or adjusted under 35 U.S.C. 154(b) by 1400 days.

This patent is subject to a terminal disclaimer.

(21) Appl. No.: 11/805,710

(22) Filed: May 24, 2007

(65) Prior Publication Data

US 2007/0286826 A1    Dec. 13, 2007

(51) Int. Cl.
| | |
|---|---|
| *A61Q 17/04* | (2006.01) |
| *A61K 8/67* | (2006.01) |
| *A61K 8/92* | (2006.01) |
| *A61K 8/98* | (2006.01) |
| *A61K 8/27* | (2006.01) |
| *A61K 8/29* | (2006.01) |
| *A61K 8/02* | (2006.01) |
| *A61K 8/06* | (2006.01) |

(52) U.S. Cl.
CPC ............ *A61Q 17/04* (2013.01); *A61K 8/025* (2013.01); *A61K 8/0241* (2013.01); *A61K 8/06* (2013.01); *A61K 8/27* (2013.01); *A61K 8/29* (2013.01); *A61K 8/678* (2013.01); *A61K 8/922* (2013.01); *A61K 8/988* (2013.01); *A61K 2800/412* (2013.01); *A61K 2800/70* (2013.01)

(58) Field of Classification Search
CPC ........ A61Q 17/04; A61K 8/678; A61K 8/922; A61K 8/988; A61K 8/27; A61K 8/29; A61K 8/025; A61K 8/06; A61K 2800/412; A61K 2800/70
USPC .......................................................... 424/59
See application file for complete search history.

(56) References Cited

U.S. PATENT DOCUMENTS

| | | | | |
|---|---|---|---|---|
| 5,085,856 | A * | 2/1992 | Dunphy et al. | 424/64 |
| 5,518,736 | A * | 5/1996 | Magdassi et al. | 424/451 |
| 5,817,298 | A * | 10/1998 | Galley et al. | 424/59 |
| 5,980,871 | A * | 11/1999 | Lukenbach et al. | 424/59 |
| 6,866,841 | B2 * | 3/2005 | Grune | 424/59 |
| 2005/0042186 | A1 * | 2/2005 | Zahner | 424/59 |

OTHER PUBLICATIONS

WideSpread Pollutants with Endocrine-disrupting Effects. [online]. Our Stolen Future, 2003 [retrieved on May 31, 2011]. Retrieved from the Internet: <URL:http://web.archive.org/web/20030210114454/http://www.ourstolenfuture.org/Basics/chemlist.htm>, 6 pages.*

* cited by examiner

*Primary Examiner* — John Pak
*Assistant Examiner* — Andriae M Holt
(74) *Attorney, Agent, or Firm* — ePatentManager.com; Guerry L. Grune

(57) ABSTRACT

The disclosure also describes a method for creating a composition, comprising: a) preparing a water phase mixture with a base of deionized water; b) optionally adding thickening or thinning agents into a water phase and mixing until free from lumps; c) optionally adding carrageenan into the mixture and mixing until free of lumps; d) heating the mixture to up to 80° C.; e) adding vegetable glycerin and optionally aloe vera gel or liquid and mixing until completely uniform; f) preparing an oil phase mixture by heating one or more carrier oils to up to 75° C.; g) adding a dispersant, SPF boosting oils and/or waxes, and optionally stearic acid, an anti-oxidant, and vitamin E oil, and mixing until all the solids are dissolved; h) slowly adding sucrose stearate, maintaining temperature; i) adding inorganic sunblock agents while homogenizing until smooth and uniform; j) increasing the temperature to up to 80° C. and adding said water phase mixture; k) mixing until smooth and homogenous; l) cooling the mixture down to 45° C. or less; m) adding aloe vera gel, and optionally a salt, grapefruit seed extract, and ascorbyl palmitate, powdered butter milk, and powdered milk; n) adding preservatives; o) adding essential oils; and finally p) mixing until smooth and homogenous. The compositions of the present disclosure are shown to be capable of protecting skin and mammalian health from the harmful effects of radiation including ultraviolet light or sunlight by inhibiting the loss of skin immunocompetency and eliminating any known or suspected endocrine disrupting agents normally utilized as sun protective agents.

9 Claims, 2 Drawing Sheets

NONTOXIC, NON-ENDOCRINE DISRUPTING, CYTOPROTECTIVE, UV-RADIATION RESISTANT SUNBLOCK COMPOSITIONS

FIELD OF DISCLOSURE

This disclosure relates to new and useful ultraviolet radiation protective agents that can be used as beneficial sunscreens and sun-blocks in various compositions or formulations, specifically those of a high SPF value (15-30, or greater). The compositions include enhanced protection and increased immuno-responsiveness by providing cytoprotective additives for mammalian skin while also providing avoidance from endocrine disrupting agents. It has been determined that sunscreen agents used in almost all currently marketed and sold ultraviolet protective compositions are essentially void of any cytoprotective agents and essentially all (both active and non-active substances) also contain suspected or documented endocrine disruptive agents.

A specific test methodology (biological based) is now available to determine not only if the substances and resulting composition possesses endocrine disrupters, but also determine the relative strength or concentration of the endocrine disrupter in a specific formulation.

BACKGROUND OF THE DISCLOSURE

Although a tan has long been considered a symbol indicative of good health and the ability to secure sufficient leisure time to enjoy many and numerous outdoor activities, it has become very evident that excessive exposure of the human skin to sunlight is harmful.

It is well documented that human skin, and most likely most mammalian skin, is sensitive to sunlight and artificial light containing radiation of wavelengths between about 290 nanometers (nm) and 400 nm. Ultraviolet radiation of wavelengths between about 290 nm and 320 nm (UV-B region) has been known to rapidly produce damaging effects on the skin including reddening or erythema, edema, blistering or other skin eruptions in more severe cases. Prolonged or chronic exposure to radiation in this wavelength range has been associated with serious skin conditions such as actinic keratoses and carcinomas. In recent years, concern has also been expressed regarding ultraviolet radiation of wavelengths above 320 nm (UV-A region) and the adverse effects of such radiation on human skin. The radiation between 320 and 400 nm also contributes to the premature aging of the skin. In addition, recent studies indicate that chronic sun exposure limits the immuno-response of the skin. There is some evidence that a tan will offer some protection against burning but that the tan is quite ineffectual against many other types of solar damage and there is no evidence that a tan increases immuno-responsive function in human skin.

Growing public awareness that the enjoyment of outdoor activities includes the need for adequate sun protection has led to an unprecedented growth in the area of sunscreen products. A study by Margaret Schlumpf from the Institute of Pharmacology and Toxicology at the University of Zurich, supports earlier health concerns regarding the use of endocrine disrupting organic substances in nearly all UV screening chemicals used in sunscreens. Additionally, the use of aloe, or more specifically aloe barbadensis Miller has heretofore been known to be a useful agent for the formulation of sunscreens as well as a substance that can both reduce UV damage to human skin that is inflamed and also promote healing. What was not well documented until recent publications and a subsequent U.S. Pat. No. 5,824,659 by Strickland and coworkers is that an extract found in all Aloe plants that is normally removed during carbon adsorptive processing, is capable of providing cytoprotection to the mammalian skin. This extract boosts the immune system response of the skin, thereby significantly reducing the risk to various forms of skin cancer. There is strong evidence to suggest that this beneficial effect translates to skin in most mammals, thereby the present disclosure provides a possible preventative formulation for animals in zoos or other habitats where UV exposure could be hazardous to the animals' health.

It is therefore desirable to provide a UV protective product that has the following attributes: protection in the UV-A and UV-B long range and short range ultraviolet radiation ranges; maintenance of coverage, i.e., waterproof and perspiration proof; application and use convenience, i.e., ease of application, invisibility, non-staining and non-greasy; and freedom from irritation as a result of its ingredients, in particular, its active sun-block or sunscreen ingredients should also be void of any known or suspected endocrine disrupters. Recent interest in this area includes some concerns over the irritancy and sensitization problems in addition to the endocrine disruptive nature that may occur in some individuals utilizing sunscreen products with high SPF values containing organic sunscreen agents. In addition, the UV protective product could also include known cytoprotective oligosaccharides from aloe barbadensis Miller preventing damage to the skin immune system caused by harmful UV radiation. "Cold-pressed" Aloe which contains the beneficial oligosaccharides and provides an emollient base for the UV protective formulation is possibly the best known choice as a cytoprotective agent that inhibits the loss of skin immuno-competency induced by ultraviolet radiation, as this agent is readily available and comparably inexpensive. Other such inhibitors are not yet well known but it is believed that amino-acids, vitamins or pro-vitamins, nucleo-derivatives, and vegetable extracts, wherein said amino acids comprise tryptophan, histidine, phenylalanine, tyrosine, said vitamins and provitamins comprise vitamin B6, vitamin A, vitamin E, tocopherols and in particular D-alpha tocopherol, beta carotene, bioflavonoids, nucleotides and polymers thereof, cascara, frangula, camomile, hyperic, calendula, elicriso, licorice or essential oils thereof all may have similar cytoprotective or immune boosting effects on mammalian skin. The essential oils of frankincense and rosemary have been found to work effectively and synergistically in strengthening the neuromuscular response of patients who are exposed to its scent in combination with compositions of the present disclosure.

One current measure of effectiveness of a sun protective product is indicated by its sun protection factor (SPF). The sun protection factor is the ratio of the amount of exposure (dose) required to produce a minimal erythema reaction in protected skin to the amount required to produce the same reaction in unprotected skin. The absolute dose differs for each human and for each mammal, and is largely dependent on genetic predisposition and ethnic origin of the human. If a human or other mammal would normally require ten minute exposure to sunlight to develop a minimal erythema reaction, then using an SPF 15 sun-block should allow for tolerance of up to 150 minutes of sunlight before developing a minimal erythema. Relatively recent public awareness of the problems of exposure to sunlight has led to a demand for sun-block products with high SPF values, i.e., at or above SPF 8.

What has not been well considered in the sun protection and cosmetics industry heretofore, is the possibility of enhancing the immuno-responsiveness of skin cells to UV light by the proper topical application such as described above by the use of extracts of aloe or similar naturally occurring substances (including kukui nut extract for example or other similar anti-inflammatory naturally occurring substances). Such substances would preferably not be processed, but if the beneficial effects are not lost during processing, then either the processed or non-processed substance may be used. The importance of processing within a short time period after harvesting the aloe plant or other plants/nuts, etc. as well as keeping the plant and subsequent plant extract cool (at or below room temperature) during processing is now well understood. Essential oils including specifically frankincense and rosemary have been shown to possibly have immuno-enhancing properties, as determined by Kinesiologist Dr. John Schmidt of Triangle Wellness Center at 182 Wind Chime Ct. Ste. 203 Raleigh, N.C. 27615. This was determined by a strengthening in neuromuscular response using scent (aroma) testing of these essential oils. The testing was performed both together with compositions of the present disclosure and alone.

Our review of the art in this field includes the following pertinent information;

For example, Japanese Patent Application No. 1981-161, 881, describes cosmetics containing 0.1-40% of ultrafine divided titanium oxide with a particle size of 10-30 nm which has been rendered hydrophobic. It indicates that when hydrophobically treated titanium dioxide with a particle size of 10-30 nm is blended into cosmetic base materials, it transmits visible light but reflects and scatters the harmful ultraviolet rays. It has been found that when these titanium dioxide compositions are utilized as a sunscreen agent in sunscreen compositions, it may result in the loss of one of the most desired properties of such compositions, i.e., invisibility.

U.S. Pat. No. 5,028,417, issued Jul. 2, 1991, describes sunscreen compositions containing microfine titanium dioxide. The particle size of the titanium dioxide is required to be less than 10 nm. It also states that other sunscreen agent can be utilized with the titanium dioxide. U.S. Pat. No. 5,340,567, issued Aug. 23, 1994 describes a sunscreen composition comprising a synergistic combination of titanium dioxide having a particle size of less than about 35 nm and zinc oxide having a particle size of less than about 50 nm with titanium dioxide and zinc oxide being present at given ratios.

German Patent No. 3642794 (1987) describes a cosmetic composition for preventing sunburn which contains 1-25% zinc oxide of a particle size of 70-300 microns. It further indicates that the composition may also contain titanium dioxide of a particle size of 30-70 microns. This composition is undesirably due to its unaesthetic whiteness characteristics at high SPF levels.

U.S. Pat. No. 5,188,831, issued Feb. 23, 1993, describes sunscreen compositions wherein the sunscreen effect is obtained from a blended of oil-dispersible ultrafine titanium dioxide and water dispersible titanium dioxide. However, the SPF level obtained is only of 10 with a total concentration of titanium dioxide of 5.0% w/w.

World Patent Application WO 90/06103, published Jun. 14, 1990, describes titanium dioxide sunscreen where the microfine titanium dioxide particles are coated with a phospholipid, either through the use of a powder mill or through the making of a dispersion in an oil phase containing the phospholipid with a high shear mixer. The phospholipid coated titanium dioxide is the incorporated into sunscreen compositions. A high efficiency is claimed: the data presented shows SPF values of up to 11 for a 3.75% titanium dioxide concentration and up to 25 for a for a 7.5% concentration of titanium dioxide. The use of high shear mixer or a powder mill is complicated and energy intensive process.

EP 535372 A1, published Apr. 7, 1993 describes a method of preparing sunscreens in which a dispersion of zinc oxide and/or titanium dioxide particles in an oil are formed by milling.

EP 619999 A2, published Oct. 19, 1994 describes an aqueous dispersion of particulate metallic oxide of particle size less than 200 nm mixed with an emulsifier and an oil phase and also an organic hydrophobic sunscreen to form an o/w emulsion. The resulting sun protection composition has a higher SPF than would be expected if there was only an additive effect. However, the titanium dioxide alone at 4% yielded a SPF of only 7 to about 11.

EP 628303, published Oct. 19, 1994 describes a process for preparing a sunscreen composition. It consists of mixing sunscreen particles of metallic oxide less than 200 nm dispersed in an oil with one or more emulsifier and/or organic sunscreens. The resulting sunscreen composition is claimed to have a SPF value considerably higher than expected. The high SPF is only obtained when a metallic oxide is blended with an organic sunscreen. In fact, when no organic sunscreen is used, the SPF value is only about 7.

WO 93/11742 describes sunscreen compositions comprising titanium dioxide and iron oxide of particle size less than 200 nm preferably coated with a phospholipid.

An article published in DCI in September 1992 by Tioxide Specialties Ltd. Describes ways of incorporating oil or water dispersions of titanium dioxide in emulsions. However, no data is given on the resulting SPF values.

An article published in Cosmetics and Toiletries, Vol. 107, October 1992, describes various ways of formulating with a physical sunblock. The discussion focuses on using titanium dioxide in a dispersion or using an emulsifier which is also an effective dispersing agent for titanium dioxide. It states that SPF's far above 20 can be achieved. However, no examples are given, nor does the article mention the specific sunscreen components or their composition.

A brochure published by the Tioxide Company on Mar. 15, 1994, discloses inorganic sunscreens of high SPF values obtained without the addition of any organic sunscreens. When measured, the SPF of the sunscreen compositions was indeed that described. However, when the titanium dioxide concentration was measured, it was at least twice what was claimed.

U.S. Pat. No. 5,498,406 describes sunscreen compositions in an oil-in-water emulsion containing both organic and inorganic sunscreens and comprising long chain (C25-45) alcohols for stabilization of the emulsion. This composition relies predominately on the organic sunscreen actives. While the authors mention the use of stearic acid as a part of the oil in water composition, they teach against the use of stearic acid in stabilizing the titanium dioxide with C22-45 alcohols.

U.S. Pat. No. 6,099,825 describes sunscreen having disappearing color which is extremely useful when combined with titanium dioxide or zinc oxide. It was unexpectedly found that although the inclusion of particulate pigments in a sunscreen emulsion can render the sunscreen visually colored as it is being spread onto the skin and that the coloration will substantially disappear when the sunscreen emulsion is rubbed into the skin.

U.S. Pat. No. 6,042,813 also describes sunscreen having disappearing color indicator. The sunscreen includes at least one active sunscreen agent, at least one emulsifier, sufficient amounts of water to create the colored emulsion, and at least one oil-soluble dye that imparts color to the emulsion.

U.S. Pat. No. 6,048,517, issued Apr. 11, 2000, describes low-cost sunscreen compositions with high SPF values of at least 40. The ingredients in the sunscreen include mixtures of homosalate, octyl salicylate, oxybenzone, octyl methoxycinnamate, or avobenzone.

U.S. Pat. No. 5,770,183, issued Jun. 23, 1998, describes an emulsion that contains a water phase and an oil phase that includes active sunscreen ingredients and skin conditioning agents. The sunscreen provides an SPF greater than 30, and the particle size in the oil phase averages 2.0 Microns, providing high levels of protection from the sun while using minimum amounts of active sunscreen agents.

U.S. Pat. No. 5,492,690, issued Feb. 20, 1996, describes a method for preventing skin damage by applying a substance that includes a benzolyacetate ester and seems to describe a potential non-endocrine disrupting benzolyacetate ester that would require testing prior to use in the present inventive composition(s).

U.S. Pat. No. 5,747,010, issued May 5, 1998, describes means and methods of protecting skin from the oxidative effects of UVA radiation using a substance that contains a lipophilic anti-oxidant. Such an anti-oxidant, if proven to be non-endocrine disruptive and not to interfere with the cytoprotective qualities of the present inventive composition(s) could also be useful and beneficial.

WO 99/11236 published first in Germany and then as a WO document dated Mar. 11, 1999, describes a transparent sunscreen gel that contains methylvinyl ether and maleic acid copolymers cross-linked with decadiene.

EP 0834301, published Mar. 8, 1998, describes compositions that include glutathione liposomes combined with at least one emulsifier and are topically applied to the skin to prevent the damaging effects of UV radiation.

U.S. Pat. No. 5,914,102, issued Jun. 22, 1999, describes an oil-in-water sunscreen emulsion comprised of at least one ultraviolet-absorbing organic compound and hydrophobically-treated silica particles. The concentration of the organic compounds is at least 30 times the concentration of the silica.

U.S. Pat. No. 5,916,542, issued Jun. 29, 1999, describes a mixture comprised of natural substances that effectively protect against skin damage caused by UVA and UVB light.

U.S. Pat. No. 5,945,090, issued Aug. 31, 1999, describes a high-SPF sunscreen comprised of an algae extract, aloe vera, and tapioca powder that protects against UVA and UVB light.

U.S. Pat. No. 5,824,659 by Strickland and coworkers is that an extract found in all Aloe plants that is normally removed during carbon adsorptive processing, is capable of providing cytoprotection to the mammalian skin.

The present disclosure allows for no removal of these important constituents and the use of ZnO is not only a useful SPF inorganic sun-block agent but also a very useful inhibitor to ensure that the biological activity of the aloe barbadensis Miller in the composition of the present disclosure has a long shelf life without any biological "growth". Shelf life is another important aspect of the present disclosure, in that many "all natural" or earth grown substances require (often toxic or endocrine disruptive) anti-bacterial substances to inhibit mold or other similar organisms from "growing" in the composition during the life of the product on the shelf.

U.S. Pat. No. 5,980,871, issued Nov. 9, 1999 to Johnson and Johnson, and apparently licensed to Neutrogena, describes a sunscreen composition that includes inorganic sunscreen agents, such as titanium dioxide or zinc oxide, anionic emulsifiers, and an oil component. The composition allows for SPF greater than 10 with a titanium dioxide concentration of about 4%. This U.S. Pat. No. 5,980,871 further describes the method required to make the sunscreen.

This disclosure does not describe the use of any cytoprotective agents or the importance of providing only non-endocrine disruptive agents to the composition. In fact the patented composition teaches away from the use of ingredients other than those that are "naturally derived" or "earth grown". The product that is described in the '871 patent itself is also undesirable as it leaves a very white appearance on the skin for long periods of time, is difficult to spread, and somewhat abrasive to sensitive skin. In addition, the composition allows for the use of parabens as inactive ingredients, also recently found to be known endocrine disrupters.

In addition, the art with regard to testing for determining the concentration of endocrine disrupters has been reviewed and is summarized below:

Japanese Application No. 2001116753A2, published Apr. 27, 2001, describes a method to sensitively and simply detect an exogenous endocrine disruptor existing in environment with extremely low concentration.

Japanese Application No. 2002355079A2, published Dec. 10, 2002, describes a method for detecting a substance having the endocrine disruption actions by using the gene affected by the endocrine disruption actions and a DNA array or equivalents thereto used for the method for detecting the substance having the endocrine disruption actions.

Japanese Application No. 2003259895A2, published Sep. 16, 2003, describes an endocrine disruptor-measuring technique which uses as an indicator the change in the aromatase activity of a biosystem reflecting a state near to a living environment.

Japanese Application No. 2002365275A2, published Dec. 18, 2002, describes a diffusive gas concentration detection pipe bringing about measurement of better accuracy and higher sensitivity from a viewpoint of the subject related to a measure of an endocrine disrupter having become a problem in recent years.

U.S. Pat. Application No. 20030087324A1, published May 8, 2003, describes a method for immunologically detecting the endocrine disrupter or its degradation product and a method for immunologically concentrating the same each by using the above antibody.

WIPO Publication No. WO0026404A1, published May 11, 2000, describes a method for detecting a gene affected by an endocrine disruptor characterized by comprising preparing a nucleic acid sample containing mRNAs originating in cells, tissues or organisms, which have been brought into contact with a sample containing the endocrine disruptor, or cDNAs thereof; hybridizing the nucleic acid sample with DNA alleys wherein genes which might be affected by the endocrine disrupter or DNA fragments originating in these genes have been fixed; and then comparing the thus obtained results with the results obtained by using another nucleic acid sample originating in a comparative sample to thereby select the gene affected by the endocrine disruptor.

SUMMARY OF THE DISCLOSURE

This disclosure relates to new and useful ultraviolet radiation protective agents in combination with lotions, cremes, pastes, sprays, lip balms, etc. that can be used as beneficial sun-blocks and in a specific instance as sunscreens in various compositions or formulations. The compositions include enhanced protection and increased immuno-responsiveness by providing cytoprotective additives for mammalian skin while also providing avoidance from endocrine disrupting agents. It has been determined at least as early as July 2001, that sunscreen agents used in almost all currently marketed and sold ultraviolet protective compositions are essentially void of any cytoprotective agents and contain suspected or documented endocrine disruptive additives in both the active and non-active ingredients. To ensure that there are no endocrine disrupters in the product, the disclosure adopts a relevant bioassay (or test method), which can both detect these chemicals (endocrine disrupters), as well as provide a relevant estimate of their endocrine disrupting potency.

It is desirable in the present disclosure to provide improved sunscreen and sun-block agents and compositions. Review of the literature, and currently marketed compositions reveal that there exists an unnecessary potential risk to human health (or other mammals) with the current commercially available formulations on the world-wide market.

It is desirable in the present disclosure to provide sunscreen compositions containing sunscreen agents that overcome the disadvantages of heretofore available compositions and to provide non-endocrine disruptive, adequate, safe protection for mammalian skin while also enhancing the skin's immuno-responsiveness from cancerous or pre-cancerous skin cells in the presence of radiation such as UV light or sunlight.

Another desirable portion of this disclosure addresses the potential risks and disadvantages, provides a viable and economically attractive alternative to the present commercial market, and proposes a new and safer rating system to rank these products for the consumer.

Another desired feature of this disclosure is to provide a method and the know-how relating to developing an "all-natural" and primarily all earth-grown ingredient based dispersion of inorganic sun-block agents that will ensure an SPF value of at least 15 or greater. The dispersion itself must not have any endocrine disrupting agents or known toxins within the composition. The sunblock may also be translucent or transparent upon application to human skin but at higher SPF levels where higher concentrations of pigments may be necessary, translucency may not be completely achievable.

Another desired feature of the disclosure is to provide a test method for determining whether there are any endocrine disrupting ingredients, active or inactive, in this sunscreen or sun-block compositions or any other composition.

Another feature of the disclosure is to adopt a test method (Applied-Kinesiology) for determining the impact that the composition has on the wearer's neuro-muscular response.

Another attribute of the disclosure includes providing the adopted test method (LUMI-CELL) to ensure that all ingredients used in the sunblock composition, both active and inactive, are non-endocrine disrupting. In addition, the muscle testing diagnosis (of Applied-Kinesiology) can be used to determine the composition's effect upon the Neuro-muscular response and the combination of such is part of the present disclosure.

Still another feature of this disclosure is to provide a reliable, convenient and relatively inexpensive technique and test methodology to determine and rank estrogenic potential and thus endocrine disruptive activity for any composition developed for skin care.

The foregoing objects and other features and advantages of the present disclosure are achieved by sunscreen and sun-block compositions containing inorganic sun-block agents or known non-endocrine disruptive sunscreen agents as the active ingredients. More particularly, the present disclosure relates to sun-block compositions containing zinc oxide and, optionally, titanium dioxide of preferred particle size ranges, and in preferred amounts and ratios. These sun-block agents together with preferably specifically cold-pressed aloe that contains an oligosaccharide of molecular weight of approximately 1-5,000 Daltons that is glucose rich and also contains mannose which inhibits the loss of skin immuno-competency form the basis of a novel protective UV formulation. It has become evident that cold-processed aloe that is processed within 45 minutes of harvesting contains about 200 biologically active agents. The synergistic effect of all of these agents is desirable and preferred to further enhance the cytoprotective ability inherent in aloe plant extract.

These specific compositions permit the possible use of much lower amounts of the sunscreen active ingredients than previously achievable while still achieving desired and very high SPF values for the compositions and without the unsightly whiteness which occurs in prior sunscreen compositions at concentrations above about 5%. In the sunscreen compositions of this disclosure, considerably higher concentrations of zinc oxide and possibly titanium dioxide may also be used without incurring a whitening effect, e.g., even up to 25% each, with acceptable appearance.

Furthermore, our disclosure does not rely upon the use of hydrophilic titanium dioxide preparations as required in the above noted patents, nor are energy intensive processes such as powder milling, nor are organic active sunscreens required for high efficacy.

The compositions of this disclosure include emulsions containing at least the following components:
(a) an inorganic sun-block agent and/or a non-endocrine disruptive sunscreen agent;
(b) a non-endocrine disrupting and cytoprotective emulsifier or mixtures thereof;
(c) an oil component comprising a carrier oil, preferably an essential oil any of which are also non-endocrine disruptive and;
(d) at least one emollient, where said emollient may be the cytoprotective emulsifier of (b) above
(e) optional sun boosting additives that are non-endocrine disruptors.

The term 'cytoprotective' refers to the ability to protect cells from becoming pre-cancerous or cancerous.

The emollient is preferably aloe as it is "cold pressed" or an extract of aloe that is currently removed during normal processing and recovered by some means. The aloe or its extract may not provide sufficient emulsification based on the remaining ingredients of the composition. It has since been determined that a single species of aloe is preferred and best for providing a healthy and well dispersed product with the highest known concentrations of cytoprotective agents—aloe barbadensis Miller-Stockton. Aloe is available in gel and in oil forms. It may also be possible to use a liposome or phospholipid such as Phosphatidyl-choline (PC), described below.

An emulsifier (also known as a surfactant from surface active material) is a substance, which stabilizes an emulsion. An emulsion is a mixture of two immiscible (unblendable) substances. One substance (the dispersed phase) is dispersed in the other (the continuous phase). Examples of emulsions include butter and margarine, mayonnaise, the photo-sensitive side of film stock, and cutting fluid for metalworking. In butter and margarine, a continuous lipid phase surrounds droplets of water (water-in-oil emulsion). Emulsification is the process by which emulsions are prepared. Examples of emulsifiers are egg yolk (where the main emulsifying chemical is the liposome or phospholipid lecithin), and mustard, where a variety of chemicals in the mucilage surrounding the seed hull act as emulsifiers; proteins and low-molecular weight emulsifiers are common as well. Whether an emulsion turns into a water-in-oil emulsion or an oil-in-water emulsion depends of the volume fraction of both phases and on the type of emulsifier. Generally, the Bancroft rule applies: emulsifiers and emulsifying particles tend to promote dispersion of the phase in which they do not dissolve very well; for example, proteins dissolve better in water than in oil and so tend to form oil-in-water emulsions (that is they promote the dispersion of oil droplets throughout a continuous phase of water).

Emollients are substances, which soften and soothe the skin. They are used to correct dryness and scaling of the skin. The terms 'moisturizer' (to add moisture) and 'emollient' (to soften) are sometimes used interchangeably as they describe different effects of these agents on the skin. However, the term emollient is most often used to describe single ingredients, whereas 'moisturizer' describes finished products. Emollients have three basic actions: 1) Occlusion—providing a layer of oil on the surface of the skin to slow water loss and thus increase the moisture content of the stratum corneum. 2) Humectant—increasing the water-holding capacity of the stratum corneum. 3) Lubrication—adding slip or glide across the skin.

An example of an emollient that will boost the occlusivity of the present disclosure is chitosan. Chitosan is a linear polysaccharide composed of randomly distributed β-(1-4)-linked D-glucosamine (deacetylated unit) and N-acetyl-D-glucosamine (acetylated unit). Chitosan is produced commercially by deacetylation of chitin (can be produced from chitin also), which is the structural element in the exoskeleton of crustaceans (crabs, shrimp, etc.). Chitosan enhances the transport of polar drugs across epithelial surfaces, and is biocompatible and biodegradable. Purified qualities of chitosans are available for biomedical applications. Chitosan and its derivatives such as trimethylchitosan (where the amino group has been trimethylated) have been used in non-viral gene delivery. Trimethylchitosan, or quaternised chitosan, has been shown to transfect breast cancer cells. As the degree of trimethylation increases the cytotoxicity of the derivative increases. At approximately 50% trimethylation the derivative is the most efficient at gene delivery. Oligomeric derivatives are relatively non-toxic and have good gene delivery properties The compositions of this disclosure provide formulations having an SPF of at least 10, with titanium dioxide, zinc oxide, or a combination of the two (with or without silica or silicon dioxide and/or cosmetic microspheres), with a treated or untreated hydrophilic surface, at concentration levels of at least 4% and preferably at least 14% to reach SPF 15 or greater. The compositions of this disclosure exhibit extremely efficient uses of sunscreen components, particularly zinc oxide. Alternatively, higher levels of preferably micronized titanium dioxide or zinc oxide can be used if ultramarine pigments are added to the composition. These pigments are known to eliminate the whiteness and poor spreadability of currently available compositions. For the purposes of this disclosure, however, these pigments must be known to be non-endocrine disruptive as well as to not interfere with the cytoprotective influence of the oligosaccharide aloe extract. The sun-block agent inorganic/organic dispersion can be made in the following way:

Essentially, the compositions of this disclosure are easily made by simple mixing and provide an excellent dispersion of the inorganic based sunscreen/sunblock agent throughout the composition, thus ensuring even skin coverage. With the use of ultramarine pigments, after initial coloring effects, the compositions are substantially invisible upon application to the skin.

Thus, in one possible embodiment, the present disclosure is directed toward a colored sunscreen emulsion comprising: (a) at least one ultramarine pigment that imparts a color other than white to the emulsion with a titanium dioxide or zinc oxide or possibly fumed or fused silica or even silicon dioxide or micronized glass cosmetic spheres so that when the emulsion is rubbed into the skin, the color substantially disappears; (b) at least one sunscreen active agent in an amount effective to protect skin against the actinic radiation of the sun—this preferably being ZnO or Z-Cote® (micronized particles—preferably nanoparticle sized to assure transparency); (c) no known or suspected endocrine disrupting organic substances; (d) a cytoprotective substance such as a glucose-rich mannose-containing oligosaccharide obtained from and used with aloe barbadensis Miller as the at least one emulsifier; and (e) sufficient water to form the other than a white colored emulsion; and sufficient dispersion to assure SPF of at least 15 and an SPF booster that shows no appreciable toxicity.

The amount of the ultramarine pigment in the composition can range from about 0 to about 25 weight percent of the composition, and preferably from about 1 to about 5 weight percent of the final formulation.

Optionally, the sunscreen emulsion can contain one or more additional ingredients, including emollients, waterproofing agents, dry-feel modifiers, insect repellants, antimicrobial preservatives and/or fragrances.

In another embodiment, the present disclosure is directed towards a method for protecting the skin against sunburn while increasing mammalian skin cell immuno-response to cancerous skin cells while eliminating possible endocrine disruption response of human organs comprising topically applying the sunscreen formulation, as described above, to the skin.

An advantage of the present disclosure is that it provides a sunscreen and a method for protecting against sunburn that enables the user to apply the sunscreen more completely and uniformly to the skin, thus providing more effective protection against skin damage and homogenously enhancing cytoprotection while eliminating endocrine disruptive organics, thus providing for long term health and safety in the presence of UV light.

Another advantage of the present disclosure is that it provides a sunscreen with a color indicator which has a low fabric staining potential, and for which those stains that form can easily be removed from fabrics.

Still yet another advantage of the present disclosure is that it provides an optionally colored sunscreen and a method for protecting against sunburn that is more enjoyable for human use because of the attractiveness and appealing nature of the color indicator.

For domesticated animals, the use of matching colors may also be appealing.

This disclosure allows for the use of ultrafine ZnO particles that are invisible when applied to human skin. This "invisible" ZnO would be the primary and perhaps only sunblock "active" ingredient or could be combined with titanium dioxide and silica or silicon dioxide and cosmetic microspheres to enhance dispersion and therefore provide a higher SPF value.

DETAILED DESCRIPTION OF THE DISCLOSURE

Figure 1:
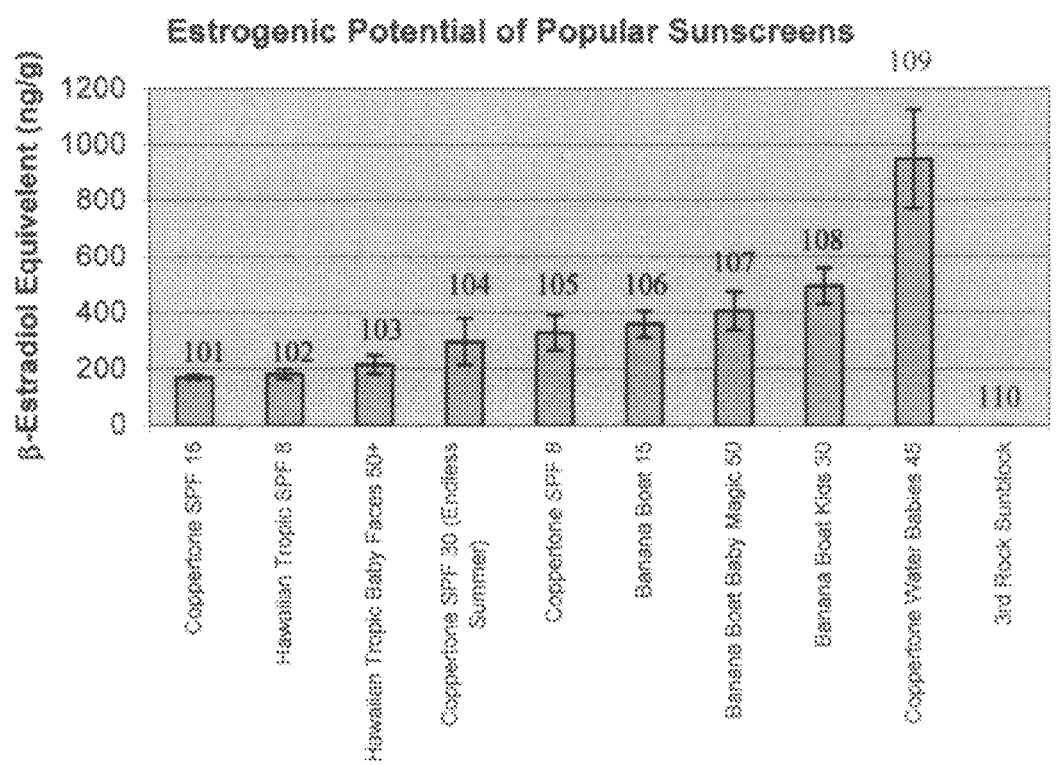
FIG. 1 provides test results for estrogenic potency (or endocrine disruptive potential) of several sunscreens currently marketed.

The UV-protective compositions of this disclosure yield highly effective ultraviolet (UV) blocking capabilities. A typical titanium dioxide sunscreen composition of SPF 15 requires levels of titanium dioxide that impart a significant whitening effect to the skin; the compositions of this disclosure minimize this disadvantage and are therefore also economically viable to produce.

The composition of this disclosure include emulsions that are cosmetically superior to conventional inorganic preparations, including water-in-oil titanium dioxide-only formulations, at equivalent SPF ratings, due to the method and type of dispersion as described above. The compositions of this disclosure can be used for sun protection in daily wear or facial products as well as for recreational situations. Because of the efficiency of the system, the inventive formulations are significantly better than the prior art in that they do not allow for any endocrine disruptive agents to be included.

There are several ingredients that contribute to the unexpectedly high efficiency of the compositions blocking of UV radiation. It has been found, however, that only one known organic UVA protector, butyl-methoxydibenzoylmethane has been shown to be benign regarding activity in cells or developmental effects on animals. Depending on the need for individual formulations based on the inventive concept herewithin, the use of this or other UVA protectors may be required. The formulation of this disclosure is intended to filter harmful UVA as welt as harmful UVB radiation so that the skin is fully protected. As each mammal's immuno-response system and skin composition is different, the required amounts required for application to the skin will vary. In addition, the actual UV protective formulation will vary based on the environmental location, length of exposure, age, health and other factors involving individual mammals, such that the concentrations of non-endocrine disruptive UVA screens, UVB screens, inorganic pigments, and cytoprotective agents will vary.

A new and unique claim of this disclosure is that the disclosure not only protects the wearer from the harmful effects of the sun but actually strengthens the wearer's 'Neuro-muscular response'. One test method, 'Applied Kinesiology', has been used to test a user's neuro-muscular response to sunblock. Applied kinesiology (AK) is a form of diagnosis using muscle testing as a primary feedback mechanism to examine how a person's body is functioning. The compositions of the present disclosure have been tested according to this response and all patients have been "strengthened" in response to the inventive composition being applied to their skin. This science is still evolving and is not fully understood and the evidence is empirical, but this testing has been performed over the course of 2 years (2004-2005) at Dr. John Schmitt's office (Triangle Wellness Center at 182 Wind Chime Ct. Ste. 203 Raleigh, N.C. 27615) and is evidentiary of the fact that the composition is, in fact, "immuno-enhancing".

A more complete rating mechanism than the SPF rating method is suggested here. The immuno-response rating system could be a simple 0-10 value, with 10 indicating a substance within a UV-protective composition that is most beneficial to boosting skin cell immune responsiveness to carcinoma, melanoma, etc. (for instance).

What has also not been well considered by the cosmetics and associated sun-protection manufacturers industry is what the effect that certain agents, recently determined to be endocrine disrupters, may have on certain mammals, particularly humans, regarding the immune system response to UV radiation. Endocrines are essentially excretions from organs or glands. The organs or glands continually function by discharging waste or at the least exchanging fluids from an inlet side to an outlet side. Any disruption in the natural behavior of an organ or gland could have a deleterious effect on the ability of that organ or gland to continue to function normally.

In a systems approach to health, the abnormal function of any organ or gland could lead to immune system disruptions (and immune system deficiencies) that may lead to serious health related complications. Changes in endocrine behavior has been strongly linked to hormonal imbalances seen in young and especially adolescent or pubescent children, as well as in the global food chain where hermaphroditic insects and other non-reproductive capable animals have been discovered.

A UV-protective formulation or composition that may inhibit normal endocrine function(s) is at least undesirable, and at most a potential health threat to millions who continue to apply such a formulation or composition directly to their skin. Although the SPF value may be high, the potential for endocrine disruption from existing formulations utilizing higher concentrations of active sunscreen agents may also be high and again this poses the possibility of another ranking system. In ranking potential endocrine disruption substances, again the 0-10 rating has appeal, with 0 being the desired criteria that a consumer would want to purchase to ensure consumption of a quality product that is also completely safe in terms of potential adverse health effects regarding the endocrine disrupters.

Therefore, as part of the present disclosure, a rating system for UV-protective compositions is proposed that includes;

SPF value—15 or greater desired

Immuno-responsiveness factor (IRF)—5 or higher desired (greater than 0)

Non-endocrine disrupter factor (NED)—0 desired

This rating system has particular relevance to the newly discovered methods reported here required to process a dispersion capable of ensuring an SPF 15 or greater value without sacrificing the need to retain an "all earth grown" or "all natural" composition.

The industry currently formulates using "pre-fabricated" dispersions in that the dispersions are purchased from a secondary source and mixed in with existing lotions, pastes, cremes, etc. This technique is unacceptable and teaches away from this disclosure, in that the dispersions themselves contain endocrine disrupters and generally toxic (cell killing) chemicals so that manufacturers cannot claim an "all natural" composition.

Therefore the ultimate UV-protective formulation would safely block or screen UV light, enhance the immune responsiveness of the skin in the absence or presence of UV, and ensure the user that there is no endocrine disrupting substance present.

Ease of application and cosmetic appeal, on the other hand, are important in formulating sunscreen compositions. These characteristics rely on subjective evaluations such as visual and tactile impression by the user. Consumer research studies indicate that a sunscreen formulation should rub in easily, leave the skin non-sticky and, above all should be invisible or at least translucent on the skin after application. Sunscreen compositions containing organic sunscreen agents have been found, in some cases, to irritate the skin. Additionally, recent studies have confirmed the suspicion that endocrine disrupting agents exist in currently available sunscreen formulations including; benzophenone-s, homosalate, 4-methyl-benzylidene camphor, octyl methoxycinnamate, and octyl-dimethyl-PABA. All of these substances, in fact, made cancer cells grow more rapidly and three caused developmental effects in animals. Therefore a non-endocrine disrupting UV protective formulation should include the use of inorganic sun-block agents. A recent development in the reduction of particle sizes of ZnO has resulted in microfine essentially clear ZnO when applied to the skin. Formulation in the family known as Z-Cote® which is a trademarked composition sold by BASF is one such example of a micronized zinc oxide available today. (The process of micronization refers to breaking up a substance into particles that are only a few micrometers in substance.) The groups of inorganic sun-block agents includes titanium dioxide, micronized titanium dioxide, zinc oxide, micronized zinc oxide, iron oxide, silicon dioxide, magnesium oxide, manganese oxide, silica, alumina, and aluminum oxides. Cosmetic microspheres, such as those made of silica dioxide or silica such as CM-111 AS produced by 3M Corp of St; Paul, Minn., can also be used as an inorganic sun-block agent.

In addition, the need for an acceptable emollient that reduces the negative affects associated with abrasive inorganics and that also includes the benefit of providing cyto-protection and healing of the skin is necessary. Allowing for the reduction of irritation or sensitization of the skin suggests that "cold-pressed" Aloe is a useful and necessary ingredient for such a UV-protective formulation.

It has also been determined that it is quite difficult, if not impossible, for current dispersion systems for micronized $TiO_2$, $ZnO$, $SiO_2$ and the like to be endocrine-disruptor free. As discussed below, the endocrine disrupters in the Lumi-cell test technique have been found to kill cells. Therefore, in essence, using one of several definitions of toxicity—adverse effects occurring as a result of repeated daily dosing of a chemical or exposure to the chemical, for part of an organism's lifespan—the dispersions themselves are toxic. The present disclosure includes the possible use of aloe, not only as an emollient, but also as a very effective dispersing agent for the inorganic micronized (and larger) sunblock active agents. High speed shearing (accomplished in a Waring blender for example), followed by high speed mixing (up to 2000 rpm with an IKA mechanical stirrer for example) provides a consistent, usable, and easily blendable inorganic/organic dispersion free of any known toxic substances (if the aloe source and inorganic particle source is well documented and controlled). The dispersion is essential in providing sufficient homogeneity and SPF values with any associated non-active cream, lotion, gel, spray, etc. that is used to provide a formulation consistent with the basis of the present disclosure.

To provide the proper SPF value, it is also necessary to enhance or boost the SPF number using boosting agents. These also may not be endocrine disrupters or toxic (cell-killing) or both. It is likely that many natural oils and perhaps derivatives of other natural occurring substances (such as essential oils of safflower, sunflower, rice bran, eucalyptus, rosemary, peru balsam, olibanum, orange, almond, sesame, ylang ylang, jojoba, or coconut) that can provide dispersion capabilities to enhance SPF may be determined to be free of endocrine disrupting capabilities. It has also been suggested that to increase SPF values for both in vivo and in vitro testing, film forming properties are important. The following film forming agents may also be used in the present disclosure: wheat protein extract, silk protein, galactoarabian, marine collagen, pea extract, purcellin oil, preen oil, wild mango butter, etc.

Bentonite can be used to boost SPF values. Colloidal Bentonite contains the active constituent montmorillonite super-refined with demineralized water as a vehicle. The liquid bentonite was the first of its kind to be processed removing the dirt, mica and impurities leaving the active ingredient Montmorillonite in a colloidal suspension. The Montmorillonite molecule has a shape similar to a business card with the wide surfaces negative and the edges of the card positively charged. This allows it to have many times more negative than positive charges. In addition, the very minuteness of the particles of Montmorillonite provides a large surface area in proportion to the volume used, thus enabling it to pick up many times its own weight in positively charged particles. To obtain maximum effectiveness in the human body, it must be put in a liquid colloidal-gel state. When a volcano erupts, there is often a fine steam or mist released which contains a substance known as volcanic ash. Bentonite is a volcanic ash. As it contains many minerals (24 to 33), it serves to mineralize the soil. Bentonite clay can be mined from veins, which are two to three feet wide and deep, but many yards long. Natives on every continent have used volcanic ash for centuries both internally and externally. The value of montmorillonite (the active ingredient in bentonite) lies in its ability to adsorb (not absorb) many times its own weight and volume in an aqueous medium. It has a predominantly negative charge that is capable of attracting many kinds of positively charged particles. Its negative charge enables it to pick up positively charged, toxic material from the alimentary canal to be expelled in the feces. The adsorption is a rapid process and can quickly neutralize allergens before they attach themselves to blood cells, thus preventing allergic reaction.

Aloe Vera gel serves numerous purposes in the present disclosure, including acting as a dispersant, as an emollient, boosting the SPF value, and improving aesthetics, and is believed by many to have healthful benefits. For medicinal purposes, aloe vera is most commonly used externally to treat various skin conditions, and burns. Not only does it soothe the skin, ease pain and reduce inflammation, studies have been done to show that using aloe as a topical treatment for burns will help speed up the healing recovery process. Many cosmetic companies are now adding this plant to products including makeup, soaps, sunscreens, shampoos and lotions, as well as any product that is created to soothe, protect and moisturize the skin. This is due partially to the fact that aloe extract is full of vitamins, nutrients and minerals.

A preferred embodiment of the present disclosure includes the use of a pure strain of aloe-vera known as aloe barbadensis Miller-Stockton. This strain or species of aloe is believed to have low concentrations of the enzyme aloin.

Aloin is an enzyme which when taken internally has a diuretic effect (i.e. it causes diarrhea) by causing inflammation within the human intestinal tract. The Stockton strain is believed to be low in aloin because the product is marketed for internal consumption and has not had any documented diuretic effect on thousands of users over the course of more than 30 years. Further, the Stockton strain is believed to include a greater concentration of cytoprotective oligosaccharides. Utilizing the Stockton strain of aloe for the formulations of the present disclosure ensures purity, uniformity, and a proper medium for dispersing the active inorganic sun-block agents. Further, the Stockton strain is ideal because it is a single species source and therefore reproducible on a batch-to-batch basis. The Stockton strain is not mixed with any other strains of aloe which are known to possess large doses of aloin or other impurities including toxic and even poisonous constituents if consumed. Further, the Stockton strain is 'cold-pressed' mechanically and not processed chemically by carbon adsorption or any other chemical means. The aloe processing industry includes carbon adsorption to prevent color loss. However, the carbon adsorption process also removes some or all of the cytoprotective oligosaccharides which the present disclosure requires. By using a single species of aloe, it is also possible to maximize the most advantageous health features of the plant (minimize any unhealthy features) used in any of the compositions of the present disclosure.

The continued and growing concern regarding estrogenic potency of sunscreens and their components associated (non-active) components has led to recent studies reviewing the "active" components of sunscreens such as 3-(4-methylbenzylidene) camphor (4-MBC), Octyl-Methoxycinniamate, and Benzophenone-3 have shown them to be highly estrogenic in assays such as uterine wet weight, cell height, and cell proliferation assays (see for example Janjua, N. R., Mogensen, B., Andersson, A-M., Petersen, J. H., Henriksen, M., Skakkebaek, N. E., and Wulf, H. C. (2004). J. of Invest. Dermatol. 123:57-61; Schlumpf M, Jarry H, Wuttke W, Ma R, Lichtensteiger W. (2004). Toxicology. 199(2-3): 109-120; Schlumpf M, Cotton B, Conscience M, Hailer V, Steinmann B, Lichtensteiger W. (2001). Environ Health Perspect. 109 (3):239-44; Inui M, Adachi T, Takenaka S, Inui H, Nakazawa M, Ueda M, Watanabe H, Mori C, Iguchi T, Miyatake K. (2003). Toxicology. 194(1-2):43-50; and Jarry H, Christoffel J, Rimoldi G, Koch L, Wuttke W. (2004). Toxicology. 205(1-2):87-93.).

Studies by Janjua et al. (2004) have shown these compounds in urine and blood plasma after topical application. Janjua et. al. (2004) also found changes in hormone (estradiol and testosterone) levels of participants after topical application.

As alluded to before, the association between the exposure and bioaccumulation of endocrine disruptor chemicals (EDCs) and their adverse effects on human and wild life populations has raised concern worldwide (see for example Jarry et al (2004); Jefferson W. N., Padilla-Banks E., Clark G., and Newbold R. R. (2002). J Chromatogr B Analyt Technol Biomed Life Sci. 777:179-189.). Due to the detrimental effects of environmental exposure to EDCs, there is an obvious need to develop a relevant bioassay, which can both detect these chemicals, as well as provide a relevant estimate of their endocrine disrupting potency. Some examples of the effects of EDCs are: decreased reproductive success and feminization of males in several wildlife species; increased hypospadias along with reductions in sperm counts in men; increase in the incidence of human breast and prostate cancers; and endometriosis (see for example Markey C. M., Coombs M. A., Sonnenschein C., and Soto A. M. (2003). Evol Dev. 5:67-75; Safe, S. H. (2002). Health Perspect. 110: 925-929; and Rogers J. M, and Denison M. S. (2000). In Vitr Mol Toxicol. 13:67-82), because these chemicals are ubiquitous, highly lipophilic, and often chlorinated, this ensures their persistent presence in the environment resulting in their bioaccumulation in the food chain.

In May of 2002 Xenobiotics Laboratories (XDS) of Durham, N.C. submitted preliminary data to ICCVAM for review as a validated regulatory method using their LUMI-CELL™ ER bioassay in response to the Federal Register Notice (Vol. 66, No. 57/Friday, Mar. 23, 2001) as a HTPS method for estrogen active compounds (see Current Status of Test Methods for Detecting Endocrine Disruptors: In Vitro Estrogen Receptor Transcriptional Activation. <//iccvam.niehs.nih.gov/docs/doc.htm> and <iccvam.niehs.nih.gov/methods/endodocs/final/ertaall.pdf> In March of 2004 SACATM gave the LUMI-CELL™ ER bioassay a high priority for validation. In April 2004 the final report on the assay was given to ICCVAM. In March 2005, ICCVAM entered the LUMI-CELL™ ER bioassay into a double blind international validation study using one lab in the European Union, Japan, and the United States. Next, studies were undertaken in which XDS's LUMI-CELL™ ER estrogenic cell bioassay system was used for high throughput screening (HTPS) analysis sunscreens. The results demonstrate the utility of XDS's BG1Luc4E$_2$ LUMI-CELL™ ER bioassay HTPS system for screening cosmetics for estrogenic/antiestrogenic activity.

There has been a growing need for a fast, reliable, inexpensive method to detect EDCs (endocrine disrupters) in the environment. As part of the present disclosure a fast, reliable, relatively inexpensive high throughput cell based recombinant bioassay screening method (LUMI-Cell™ ER bioassay) to determine the level of xenoestrogenic EDCs was reported.

Sunscreen components were purchased from the Inolex Chemical Co., Goldschmidt Chemical Corp., Kobo Products Inc., and Dow Corning. Sunscreens were purchased at Wal-Mart.

LUMI-CELL™ ER Bioassay. The BG1Luc4E2 cell line was constructed as previously described by Rodgers and Denison (2000). Briefly, BG1 cells were stably transfected with an estrogen-responsive luciferase reporter gene plasmid (pGudLuc7ere) and selected for using G418 resistance (see Rogers et al (2000)).

Cell Culture and Bioassay Plates. BG1Luc4E2 cells were grown in RPMI 1640. The cells were transferred into flasks containing DMEM media (supplemented with 5% carbon stripped fetal calf serum and G418 sulfate solution), and incubated for four days before harvesting for BG1Luc4E$_2$ bioassay plates. The cells were then plated in 96 well plates and incubated at 37° C. for 24-48 hours prior to dosing.

Endocrine Extraction Procedure: One gram of each of the lotion components and 0.5 g of each of the sunscreens was placed in MeOH rinsed scintillation vials. Two and 4-gram aliquots of the $3^{rd}$ Rock Sunblock were also tested. Twenty ml of MeOH was added to each scintillation vial and sonicated for 20 min. Fractions of these extractions, ranging from 1:10 to 1:80,000 were tested. Recoveries were determined using 10 ng 17β-estradiol spiked into $3^{rd}$ Rock Sunblock prior to extraction with 20 ml MeOH compared to 10 ng 17β-estradiol spiked into 20 ml MeOH.

Bioassay Dosing Process. Once the assay plate completed its incubation, the media solution in each well was removed and two hundred microliters of DMEM containing the indicated concentration of the desired chemical to be tested was added to each well. The plate was then incubated for 20 hours before analysis of luciferase activity.

Bioassay Analysis by Berthold Luminometer. After lysing the cells (Promega lysis buffer), the luciferase activity was measured in a Berthold Orion Microplate Luminometer, with automatic injection of 50 microliters of luciferase enzyme reagent (Promega) to each well. The relative light units (RLUs) measured were compared to that induced by the 17beta-estradiol standard after subtraction of the background activity. Each compound was tested at least three times on three different sets of plates and the EC50 value in mmol/ml was determined using the Microsoft Excel Forecast function.

In a recent study by Dr. George C. Clark, president of Xenobiotic Detection Systems Inc., several sunscreens currently marketed as well as the "non-active" sunscreen components were tested for estrogenic potency (or endocrine disruptive potential). The popular sunscreens tested include (as shown in FIG. 1): Coppertone SPF 8 105; Coppertone SPF 15 101; Coppertone SPF 30 (Endless Summer) 104; Banana Boat SPF 15 106; Banana Boat Kids SPF30 108; Hawaiian Tropic SPF 8 102; Coppertone Water Babies SPF 45 109; Banana Boat Baby Magic SPF 50 107; Hawaiian Tropic Baby Faces SPF 50+ 103; and $3^{rd}$ Rock Sunblock™ SPF 30 110. The $3^{rd}$ Rock formulation conforms to the requirements described in the present disclosure. The "non-active" components are compounds used in sunscreens and sunblocks that do not directly protect from UV damage and these include: Lexorez 200 (for water resistance) 203; ABIL Wax 9801 (improves SPF response) 202; TEGO care PS (Emulsifier) 205; ABIL WE-09 (Emulsifier—that may boost SPF) 204; KOBO CM3K40T4 (also may boost SPF) 207; Lanol 84D Dioctyl malate (allows for smooth texture—emollient/emulsifier) 206; Dow Corning 344 (Lubricant) 201; Dow Corning 1401 (Lubricant) (both silicone oils) 208.

Figure 2:
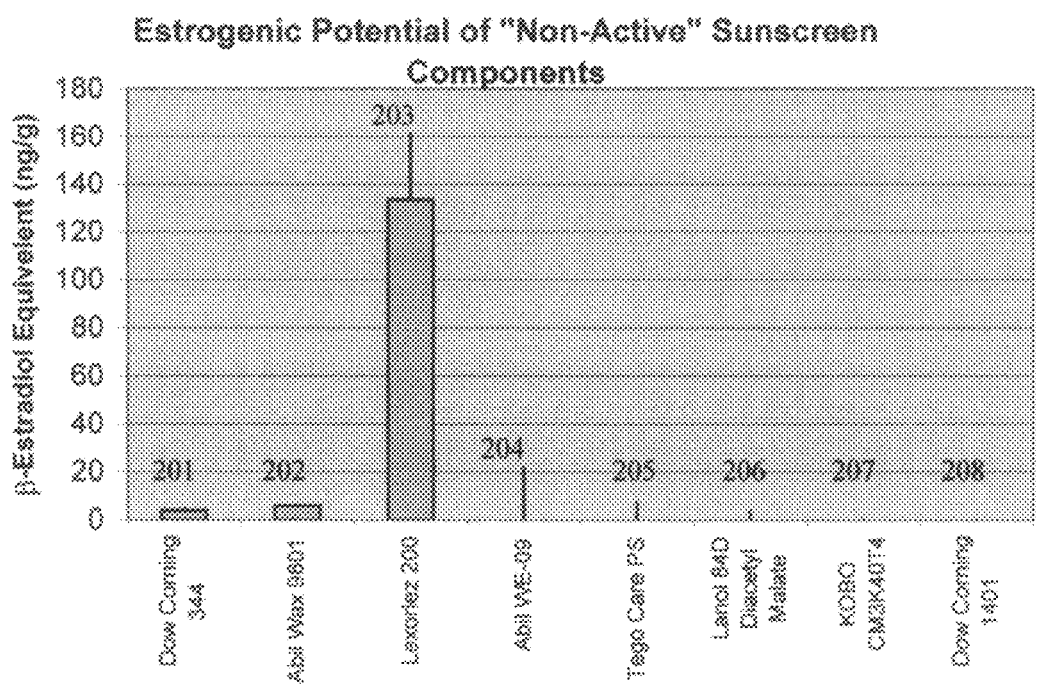
FIG. 2 provides test results for estrogenic potency (or endocrine disruptive potential) of the "non-active" sunscreen components of several sunscreens currently marketed.

The results achieved are shown in FIG. 2.

To ensure that the claims of the present disclosure have scientific basis and merit, 13 sunscreen products and 8 "non-active" lotion components were tested for estrogenic potency. The samples were tested at 4 g, 2 g, 1 g, 0.5 g, and 0.1 g. The 0.5 g aliquot was selected for sunscreens and 1 g for "non-active" components due to it showing the most activity with the least toxicity. The $3^{rd}$ Rock Sunblock SPF 30™ was used as a negative control due to it previously testing as a non-detect. The $3^{rd}$ Rock Sunblock SPF 30 was also used in recovery determinations. This was performed by dividing the average RLU for the 10 ng 17β-estradiol spiked $3^{rd}$ Rock Sunblock SPF 30 by the 10 ng 17β-estradiol spiked into 20 ml MeOH. The average recovery was found to be 77.4%. $3^{rd}$ Rock Sunblock is proprietary formulation provided for this study by G. L. Grune to Xenobiotics in 2004.

All of the sunscreens detected positive for estrogenic activity with the exception of $3^{rd}$ Rock Sunblock, which was shown as a non-detect at less than 0.308 pg/g 17β-estradiol equivalent. The sunscreen with the highest estrogenic potential was Coppertone Water Babies SPF45 at 948.66±176.62 ng/g 17β-estradiol equivalent. Based on our test results, the order of estrogenic potency appears to be: Coppertone Water Babies 45>Banana Boat Kids 30>Banana Boat Baby Magic 50>Banana Boat 15>Coppertone SPF 8>Coppertone SPF 30 (Endless Summer)>Hawaiian Tropic Baby Faces 50+>Hawaiian Tropic SPF 8>Coppertone SPF 15>$3^{rd}$ Rock Sunblock SPF 30. Results are shown in FIG. 1 above.

Only 3 of the "non-active" components showed any activity with only Lexorez 200 showing any significant estrogenic potency. The others showed very high detection limits due to their toxicity. These results are summarized in FIG. 2 above.

This study demonstrated that the "non-active" components contribute to a portion of the estrogenic potency of many sunscreen formulations. However, a significant portion of the estrogenic potency remains attributed to the "active" components of the same formulations. Further investigations will include testing "active" and "non-active" components for more detailed analysis regarding estrogenic potency ratios. It is apparent from the foregoing study and results that the test methodology enables one to determine the estrogenic potency of any skin product, not only one designed for sun protection. It is known that lotions, shampoos, cleansing agents, cremes, sprays, etc. for human and animal skin contact for various uses contain numerous endocrine disrupting components. Therefore, the present disclosure includes a test methodology to determine levels of toxicity (as defined by killing cells) that includes determining estrogenic potency and therefore also the propensity for and concentration of endocrine disruption.

The results of this study have now been published in a peer-reviewed scientific journal, demonstrating that the present disclosure has been shown not to be an endocrine disrupter, in contrast to other currently existing sunblock compositions. As reported in the 2006 Journal of the Society of Toxicology (p. 395), research conducted primarily by Dr. G. C. Clark ("Estrogenic Potency of Many Popular Sunscreens and Lotion Components Detected using the Lumi-Cell ER Bioassay") showed that "Methanol extracts of all sunscreens tested positive for estrogenic activity with the exception of 3rd Rock Sunblock. The order of estrogenic potency was: Coppertone Water Babies SPF45>Banana Boat Kids SPF30>Banana Boat Baby Magic SPF50>Banana Boat SPF15>Coppertone SPF8>Coppertone SPF30 (Endless Summer)>Hawaiian Tropic Baby Faces SPF50+>Hawaiian Tropic SPF8>Coppertone SPF15>3rd Rock Sunblock SPF20." The LUMI-CELL® ER estrogenic cell bioassay system was used for screening evaluation of 10 commercial sunscreen products and 8 lotion components. LUMI-CELL® ER bioassay consists of BG1 cells transfected with an estrogen-responsive luciferase reporter gene plasmid.

Components of the Disclosure

The compositions of this disclosure may, include one or more of a select group of anionic emulsifiers. In particular, salts of certain fatty acids are useful in the formulations of this disclosure, preferably salts of saturated fatty acids and/or salts of straight-chain fatty acids. Alkali metal salts, alkali earth metal salts and amine salts are more preferable for use in the compositions of this disclosure. For example, stearic acid and its salts are useful as emulsifiers in the compositions of this disclosure, while the use of isostearate salts tends to produce a composition which is not very efficient in the use of sunscreen. Likewise, oleate salts are not useful as they are unsaturated and do not result in efficient sunscreen compositions. Sodium borate is an example of a preferred salt.

Most preferably, the emulsifier should be sodium stearate. While it is not fully understood why some salts of fatty acids result in an improved inventive composition, it is theorized that salts of straight-chain fatty acids, (the fatty acids having a relatively high melting point, above 70° C. or higher), are preferable due to their structure.

The anionic emulsifiers should be present in the compositions of this disclosure in an amount from about 0.01 to about 10%, more preferably 0.1 to about 7% and most preferably from about 0.5 to about 5%. There may be additional emulsifiers present in the compositions of this disclosure. However at least one anionic emulsifier should be present in order to achieve the products of this disclosure. The fatty acid salt emulsifiers may be added to the composition as the salts, or the salt may be formed in situ.

Phosphatidyl-choline (PC), a phospholipid also known as lecithin and PhosChol, can be used as a natural dispersant and/or emulsifier. It is the major component of a phosphatide fraction which may be isolated from either egg yolk or soy beans from which it is mechanically or chemically extracted using hexane. It is commercially available in high purity as a food supplement and for medical uses. PC is regarded as a well tolerated and non-toxic surfactant. It is approved by the United States Food and Drug Administration for human consumption with the status "Generally Recognized as Safe". Lecithin is an integral part of cell membranes, and can be totally metabolized, so it is virtually non-toxic to humans. Other emulsifiers can only be excreted via the kidneys. Some commercially available PC products are Phospholipon 90G® and Phospholipon 85G®, distributed by the American Lecithin Company of Oxford Conn. PC can be dispersed into an oil, glycerin, aloe vera, or otherwise suitable solvent before being added into the present formulations of the present disclosure as an emulsifier or dispersant.

A liposome is a spherical vesicle with a membrane composed of a phospholipid bilayer used to deliver drugs or genetic material into a cell. Liposomes can be composed of naturally-derived phospholipids with mixed lipid chains (like egg phosphatidyl-ethanolamine), or of pure components like DOPE (dioleolylphosphatidylethanolamine). The lipid bilayer can fuse with other bilayers (e.g., the cell membrane), thus delivering the liposome contents. By making liposomes in a solution of DNA or drugs, (which would normally be unable to diffuse through the membrane), they can be (indiscriminately) delivered past the lipid bilayer.

Liposomes can be created by sonicating phospholipids in water. Low shear rates create multilamellar liposomes, which have many layers like an onion. Continued high-shear sonication tends to form smaller unilamellar liposomes. In this technique, the liposome contents are the same as the contents of the aqueous phase. Liposomes can be used as emulsifiers in the same manner as the phospholipids discussed above.

Humectants can form an important part of the present disclosure. The main purpose of any cream is to keep the skin moist. Many conventional creams form a suffocating film on the skin to prevent moisture loss. Even a natural humectant, glycerin, actually attracts water from the air and surrounding tissue. It keeps the skin moist as long as there is sufficient moisture in the air. In a dry climate it actually draws moisture from the skin. Collagen, elastin, panthenol (pro-vitamin B5) and keratin enjoy some popularity as humectants. Another example is Pepha®-Nutrix, a product of Pentapharm Ltd of Basel, Switzerland.

Natural phospholipids, or lecithin, are also an excellent humectant. An important benefit of phospholipids is that they are hygroscopic (attract water from the surrounding air) and hold water where an increased level of hydration is needed. Therefore, phospholipids increase the hydration levels of the skin without being occlusive (forming a film to prevent water loss, and preventing normal cellular function).

A carrier oil is useful in the compositions of this disclosure. There are a range of different carrier oils each with their own individual properties and suitability towards different treatments in aromatherapy. The carrier oil may be selected from the group of essential oils or other known non-endocrine disrupter esters. Other carriers include castor oil, avocado oil, broccoli seed oil, keratin, and micronized or colloidal bentonite.

Preferably, the carrier oil which is more preferably an essential oil, should be present in the composition in an amount of between about 0.1% and about 10%. More preferably, it should be present in the amount of between about 1% and about 5%. Most preferably, it should be present in the amount of between about 2% and about 4%. All essential oils are non-endocrine disrupting. Examples of essential oils include oils of jojoba, rice bran, sesame, safflower, almond, sweet almond, eucalyptus, sunflower, peru balsam, rosemary, olibanum, orange, sunflower, ylang ylang, apricot kernel, avocado, borage, cocoa butter, evening primrose, grapeseed, hazelnut, kukui, macadamia nut, olive, peanut, pecan, rose hip, bergamot, jasmine, neroli, patchouli, petitgrain, rose, vetiver, chamomile, mandarin, lavender, grapefruit, cypress, bay laurel, frankincense, clary sage, ginger, helichrysum, lemon, sandalwood, basil, black pepper, peppermint, geranium, wintergreen, thyme, tea tree, tangerine, spearmint, common sage, rosewood, pine, patchouli, oregano, nutmeg, myrrh, melaleuca, marjoram, manuka, lemon grass, lavender, juniper, ginger, cumin, clove, camphor, bay leaf, anise, allspice, and hyssop.

A number of the above mentioned essential oils, including jojoba and avocado, can be utilized in the present formulations as emollients.

For conventional UV-protection formulations, an oil phase should contain at least two materials, the carrier oil or essential oil and a conventional emollient known to those of ordinary skill in the art as useful in sunscreen products, such as mineral oils, ester oils, vegetable oils, synthetic emollients such as fatty acid esters and the like. For the present disclosure, the use of a cold pressed aloe barbadensis Miller and specifically the Stockton species is to be substituted as an emollient or can be used in combination with the oils or emollients that are proven to be non-endocrine disrupting as well as not interfering with augmenting the cytoprotective enhancing effects of the known effective oligosaccharide aloe extract. The emollient should be present in the formulation in a ratio to the carrier concentration of from about 1:1 to about 3:1, most preferably, about 2:1. The carrier oil and the emollient should compose from about 2% to about 40% of the total composition weight.

A third element which should be present in the compositions of this disclosure is an inorganic sunscreen compound, such as titanium dioxide, zinc oxide or combinations thereof. Possible other inorganics include the use of fused or fumed silica or even silicon dioxide. Preferably, titanium dioxide, zinc oxide, silica, silicon dioxide, or cosmetic microspheres should be used having a primary particle size of less than about 300 nm in diameter. It should be present in the composition in the amount of from about 2% to about 25%. More preferably, it should be present in the amount of from about 2% to about 15%. The inorganic sunscreen compound should be oil dispersible, and may be present with or without surface coating.

The ratio of titanium dioxide or zinc oxide to the weight of the carrier oil and the emollient combined should be from about 0.0:1 to about 1:1. More preferably, the ratio should be between about 0.25:1 and 2:3, and most preferably 0.33:1.

In the case where salts of fatty acids are used care should be taken to keep the pH of the compositions of this disclosure at a level above about 5, more preferably, above about 5.5. Maintaining the pH at this level will ensure that these anionic emulsifiers remain in the salt form, which is important in retaining the stability and efficacy of the composition.

Additionally, the usual elements of a modern sunscreen emulsion system may be necessary such as a polymeric thickener/stabilizer, one or more additional emollient oils, microbial preservatives, waterproofing agents, antioxidants, fragrance, humectant, and of course the water vehicle may all be utilized using careful selection or restraint based on the constraints of providing a non-endocrine disrupting immuno-enhancing composition.

The base formulation of this disclosure may also be used as carrier compositions for active topical agents having dermatological effects, including depigmentation agents, anti-aging ingredients, anti-fungal agents, anti-microbial agents, insect repellents and the like. For example, depigmentation agents can include magnesium ascorbyl phosphate or hydroquinone but only used in the final composition if these agents are shown not to be endocrine disrupters. Anti-aging agents can include retinoid compounds and alpha-hydroxy acids again only if these agents are shown not to be endocrine disrupters. Anti-fungal agents that can be included in the compositions of this disclosure include azole compounds including ketoconazole and the like again only if these agents are shown not to be endocrine disrupters. Anti-microbial agents include triclosan, an agent regarding cytotoxicity or endocrine disruption function. Insect repellant fragrances can be included in the compositions of this disclosure again only if these agents are shown not to be endocrine disrupters. Other products known to those of ordinary skill in the art may be delivered to the skin using the compositions of this disclosure.

The compositions of this disclosure would then have minimally a multi-action capability, as they would contain both sunscreen agents and other actives for protecting, treating, and enhancing the immuno-responsive nature of the skin.

The compositions of this disclosure can be incorporated into various cosmetic and personal care products such as hand and body lotions, oils, ointments, lip balm products, facial cosmetics and the like.

One of the major challenges in providing the composition of the present disclosure is to provide a non-toxic, non-endocrine disrupting, immuno-enhancing high (15 or greater) SPF formulation that can be readily achieved in a manufacturing environment for a reasonable cost. The use of aloe as both an emollient and a surfactant/dispersion agent together with either micronized ZnO, titanium dioxide, silicon dioxide, fluoropolymers, silica, etc. (inorganic or acceptable organic sun-block agents) in the manner outlined above is unique and novel. The addition of SPF boosting agents that are neither toxic nor endocrine disrupters is also unique to this disclosure and has heretofore not been seriously considered or explored.

It should be emphasized that SPF values of 15 or greater can be achieved solely by blending and subsequent mixing of aloe with vegetable glycerin (or glycerol as it is also known) and that we have achieved a superior product using this technique. This would be the so-called "aloe-water" phase that would be subsequently mixed at high speed with the so-called "oil-phase". Blending would be accomplished using either the aloe-water phase or oil phase and in so doing, the aloe would not be necessarily diluted with water until after the full addition and blending of the inorganic sun-block agents. Water dilution during or after blending is acceptable but not necessary and in some cases it may be undesirable. It is also desirable to add inorganic sunblocking agents directly to the oil phase to insure SPF values greater than 15. Often, it is necessary to add the inorganic sunblocking agents to both phases (oil and water) to provide a superior formulation.

The aloe and specifically single species of aloe as described above, seems particularly well-suited (with and without the use of glycerin) to provide an emulsion that is homogeneous and can achieve sufficient SPF values using 14% or more (by weight) of the inorganic sun-block agents. Micronized sun-block agents are best for this emulsion as they provide the best surface area-volume ratio for proper wetting of the ZnO and other micronized inorganic/organic particles.

The well known and commercially available "SPF boosters" have almost without exception proven to be toxic or endocrine disrupters or both and the present disclosure includes a scientifically accepted and peer reviewed method to assure the use of only SPF boosters that are neither toxic nor endocrine disrupters. The use of phospholipids or liposomes described above may also provided the needed oil-water dispersion and thus boost SPF.

The use of green tea extract may be effective in reducing sunburn. Green tea is a powerful antioxidant that neutralizes free radicals from UV radiation and helps protect skin cells by its photoprotective effect on human skin and its polyphenolic antioxidant contents. Green tea protection works in the cell after exposure to ultraviolet rays. Studies suggest it causes abnormal cells to kill themselves, a type of programmed cell suicide that prevents the development of abnormal growths. Green tea inhibits UVB-induced erythema response in the skin (redness reaction). At the same time it supports the production of melanin, the skin's own natural sunburn protection. Thus green tea helps reduce the risk of sunburn and boosts SPF.

Tocopherol, or Vitamin E oil, is a fat-soluble vitamin in eight forms that is an important antioxidant. Vitamin E is often used in skin creams and lotions because it is believed to play a role in encouraging skin healing and reducing scarring after injuries such as burns. Natural vitamin E exists in eight different forms or isomers, four tocopherols and four tocotrienols. All isomers have a chromanol ring, with a hydroxyl group which can donate a hydrogen atom to reduce free radicals and a hydrophobic side chain which allows for penetration into biological membranes. There is an alpha, beta, gamma and delta form of both the tocopherols and tocotrienols, determined by the number of methyl groups on the chromanol ring. Each form has its own biological activity, the measure of potency or functional use in the body. For the present disclosure, the most stable forms of Vitamin E are desired.

Rosehip, also called the rose haw, is the pomaceous fruit of the rose plant and a powerful antioxidant. It is typically red to orange but may be dark purple to black in some species. Particularly high in Vitamin C, with about 1700-2000 mg per 100 g in the dried product, it is one of the richest plant sources of the vitamin. It also contains vitamins A, D and E, and antioxidant flavonoids. Rosehip can be used as an emollient in the present disclosure. The use of vitamin C (ascorbic acid or other available forms of Vitamin C) in sunscreen or sunblock formulations should be in a stabilized form such as Magnesium ascorbyl phosphate. For the present disclosure and associated formulations, the most stable form of Vitamin C can be incorporated.

Keratins may provide an SPF boost to the present compositions. Keratins are a family of fibrous structural proteins; tough and insoluble, they form the hard but non-mineralized structures found in reptiles, birds and mammals. They are rivaled in biological toughness only by chitin, a cellulose-like polymer of glucosamine and the main constituent of the exoskeletons of arthropods. The properties which make structural proteins like keratins useful depend on their supermolecular aggregation. These depend on the properties of the individual polypeptide strands, which depend in turn on their amino acid composition and sequence. The α-helix and β-sheet motifs, and disulfide bridges, are crucial to the conformations of globular, functional proteins like enzymes, many of which operate semi-independently, but they take on a completely dominant role in the architecture and aggregation of keratins. Keratins contain a high proportion of the smallest of the 20 amino acids, glycine, whose "side group" is a single hydrogen atom; also the next smallest, alanine, with a small and uncharged methyl group. In the case of β-sheets, this allows sterically-unhindered hydrogen bonding between the amino and carboxyl groups of peptide bonds on adjacent protein chains, facilitating their close alignment and strong binding. Fibrous keratin molecules can twist around each other to form helical intermediate filaments.

Sucrose stearate is usually a white or light brown block or powder, with little or no smell and no taste. It is an exceptionally mild emulsifier derived from sugar and coconut or palm oil. Sucrose stearate is made by combining sugar with Stearic Acid. Cane sugar is a sweetening agent and food which can act as a preservative and antioxidant, and stearic acid is a natural fatty acid derived from coconut or palm oil. Because it is made from vegetable sources it is completely biodegradable. One commercially available form of sucrose stearate is Crodesta® F-160, manufactured by Croda of Yorkshire, England.

Lanolin is a thick natural moisturizer to soothe and protect skin. It is derived primarily from the oil glands in sheep's wool, also known as wool oil, wool wax, wool fat, or wool grease. Wool fat is a mixture of many different chemical compounds, including cholesterol and the esters derived from 'fatty' acids containing 18 to 26 carbon atoms. Lanolin is used in many skin formulas to prevent possible irritation from other oils. It functions as a salve and an emollient by sealing in your body's moisture, and is a natural water repellant. Lanolin forms an emulsion with water that's easily absorbed by the skin, softening it and preventing it from frying and cracking. It is used for dry skin, sunburn, and windburn, and may also boost SPF.

A number of oils are used in commercial sunblocks as SPF boosters. Such oils may be effective at boosting SPF on their own in some cases, or in combination with other oils in other cases. Among these oils are sunflower oil, safflower oil, almond oil, rice bran oil, eucalyptus oil, sesame oil, orange oil, jojoba oil, rosemary oil, peru balsam oil, grape seed oil, pomegranate seed oil, etc. Certain waxes may also have a positive SPF effect, including beeswax, orange wax, synthetic waxes and the like.

Beeswax is a product from a beehive. Beeswax is secreted by honeybees of a certain age in the form of thin scales. It is a tough wax formed from a mixture of several compounds; its main components are palmitate, palmitoleate, hydroxypalmitate and oleate esters of long-chain (30-32 carbons) aliphatic alcohols, with the ratio of triacontanylpalmitate $CH_3(CH_2)_{29}O-CO-(CH_2)_{14}CH_3$ to cerotic acid $CH_3(CH_2)_{24}COOH$, the two principal components, in a ratio of 6:1. Beeswax is used commercially to make fine candles, cosmetics and pharmaceuticals including bone wax (cosmetics and pharmaceuticals account for 60% of total consumption), in polishing materials (particularly shoe polish), as a component of modeling waxes, and in a variety of other products. For the present disclosure, the use of Hydroxyoctacosanyl hydroxystearate can not be used as a beeswax substitute as a consistency regulator and emulsion stabilizer. Japan wax is another substitute that may not be used. Beeswax's primary use in the present disclosure is to increase the water-resistant capabilities of the composition. The beeswax can also be impregnated with sun-block materials (micronized zinc oxide and titanium dioxide, etc.) in order to prevent these materials from being easily washed away during use.

Skin care products do not last forever. Just like food, all natural skin care products will eventually deteriorate. Chemical preservatives are generally used in the industry because they are much cheaper than, and extend the shelf life of the product more than, natural alternatives. The preferred preservative in the present disclosure is Biovert®, a product of Arch Chemicals®. Biovert® is a system of two linked preparations, which by themselves do not offer anti-microbial efficacy, but together offer anti-microbial efficacy. Biovert® mimics a naturally occurring antimicrobial-antioxidant protection system. When the two-part system is combined, a cascade of linked reactions takes place to generate antimicrobial products in situ. The cascade is initiated by the action of the glucose oxidase enzyme in the presence of its substrate (glucose) and oxygen. This generates $H_2O_2$, which is used by the lactoperoxidase to catalyze the oxidation of $I^-$ and $SCN^-$ anions, forming hypoiodite and hypothiocyanate which have antimicrobial activity. The result is rapid microbial cell death. Other natural preservatives include tea tree and thyme essential oils, grapefruit seed extract, and D-alpha Tocopherol Acetate (Vitamin E).

One possible method for composing the sunblock composition of the present disclosure may be performed using a two-vessel method, in which the oil and aloe or water phases are individually prepared. This process produces a smooth, uniform, white to light ivory emulsion that is satisfactory when the inorganic particles are sufficiently dispersed to provide desired SPF values. When combined with ultramarine pigments, the color will change and may also provide a clear appearance (using the micronized inorganics) as the composition is applied to the skin.

In accordance with a two-vessel process, an aloe or water phase is prepared by measuring deionized water into a receptacle and mixing. Xanthan gum is sprinkled and mixed until free from lumps. Carrageenan is then mixed in until freed from lumps. (Carrageenan could serve as an alternative to xanthan gum throughout the present disclosure.) The mixture is optionally slowly heated to approximately 80° C., although room temperature or below is preferred. Vegetable glycerin is then added, followed by aloe vera gel. The composite is mixed until completely uniform.

The oil phase is prepared separately in another vessel, at approximately 75° C. Sun-block agents comprising the following are mixed together until dissolved: refined sunflower oil, lanolin, phospholipids or liposomes, coconut oil, stearic acid, beta carotene, orange wax, beeswax, essential oils, and Vitamin E oil. When mixed, sucrose stearate is slowly added. While maintaining a temperature of 75° C., micronized zinc oxide is sprinkled very slowly and homogenized until smooth and uniform. Cosmetic microspheres and/or titanium dioxide can then be added in the same fashion as the micronized zinc oxide. The temperature of the mixture is raised to 80° C., and the water phase as described above is then added to the oil phase under heavy mixing conditions. Mixing should continue for at least 30 minutes until the mixture is smooth and homogenous. It is preferable to perform the mixing at room temperature or below.

The combined mixture can then be cooled to 45° C. or below. The following ingredients can then be individually added, mixing each well before adding another: aloe vera gel, granular borax, grapefruit seed extract, ascorbyl palmitate, butter milk powder, milk powder. Preservatives are then added and can comprise the following: Biovert® substrate, glucose, lactoperoxidase, and glucose oxidase. Essential oils, for example rosemary oil, peru balsam oil, and olibanum oil (frankincense) are then added to provide fragrance and mixed until smooth and homogenous.

An alternative method for formulating the composition is as follows: the formulation is prepared using a two-vessel method, in which the oil and aloe or water phases are individually prepared. In accordance with this two-vessel process, an aloe or water phase is prepared by measuring deionized water into a receptacle and mixing. Carrageenan is then mixed in until freed from lumps. The mixture is optionally slowly heated to approximately 80° C., although room temperature or below is preferred. Vegetable glycerin is then added, followed by aloe vera gel. The composite is mixed until completely uniform.

The oil phase is prepared separately in another vessel, at approximately 75° C. Sun-block agents comprising the following are mixed together until dissolved: jojoba oil, rice bran oil, lanolin, phospholipids or liposomes, stearic acid, orange wax, beeswax, essential oils, and Vitamin E oil. While maintaining a temperature of 75° C., micronized zinc oxide and titanium dioxide are sprinkled very slowly and homogenized until smooth and uniform. The temperature of the mixture is raised to 80° C., and the water phase as described above is then added to the oil phase under heavy mixing conditions. Mixing should continue for at least 30 minutes until the mixture is smooth and homogenous.

The combined mixture can then be cooled to 45° C. Again, it is preferable to conduct the mixing at room temperature or below. The following ingredients can then be individually added, mixing each well before adding another: aloe vera gel, grapefruit seed extract, ascorbyl palmitate. Preservatives are then added and can comprise the following: Biovert Substrate®, glucose, lactoperoxidase, and glucose oxidase. Essential oils, for example rosemary oil, peru balsam oil, and olibanum oil (frankincense) are then added to provide fragrance and mixed until smooth and homogenous.

The following examples serve as illustrations of the compositions of the present disclosure, however, they do not limit the scope of the disclosure described herein.

EXAMPLE I 211.79 ml of deionized water was added to the receptacle. 0.25 grams of xanthan gum was then added to the receptacle. The composition was mixed until free from lumps. 1.0 g of Carrageenan was added to the receptacle. The composition was mixed until free from lumps. The mixture was heated to 80° C. 15.0 grams of vegetable glycerin was then added to the receptacle, along with 15.0 g of Aloe Vera Gel. The ingredients in the receptacle were then mixed until completely uniform. In a second receptacle, 15.0 g of sunflower oil, 30.0 g of phosphatidyl choline, 1.0 g of coconut oil, 80.0 g of carrier oils, 10.0 g of stearic acid, 0.0005 g of beta carotene, 1.0 g of orange wax, 5.0 g of beeswax, and 0.5 g of vitamin E oil (tocopherol) were mixed until all solids were dissolved, and the mixture was heated to 75° C. 5.0 g Crodesta F-160® (produced by Croda USA) was slowly added, while maintaining the temperature at 75° C. 80.0 grams of micronized zinc oxide (Z-Cote®) was sprinkled in slowly and homogenized until smooth and uniform. 10.0 grams of Sensient Cosmetic Microspheres CM-111® was sprinkled in slowly and homogenized until smooth and uniform. The temperature of this receptacle was increased to 80° C. The first receptacle was then added to the second with vigorous mixing at 80° C. Mixing continued for 30 minutes until the composite was smooth and homogenous. The temperature of the receptacle was lowered to 45° C. 5.0 grams Aloe Vera gel was added, while mixing thoroughly. 0.2 g of borax granular was added, while mixing thoroughly. 5.0 grams of Grapefruit Seed Extract (GSE) was added, while mixing thoroughly. 0.5 grams of ascorbyl palmitate was added, while mixing thoroughly. 0.5 grams of milk powder and 0.5 grams of buttermilk powder were added, while mixing thoroughly. 5.25 grams of Biovert® substrate, a product of Arch Chemicals and a composite of glucose, lactoperoxidase, and glucose oxidase was then added, mixing thoroughly. 1.0 grams of rosemary oil, 0.5 g of peru balsam oil, and 1 gram of olibanum oil (frankincense) were then added. The receptacle was mixed until smooth and homogenous.

SPF (sun protection factor) can be measured as the ratio of the optical signal through the substrate without sunscreen divided by the optical signal through the substrate coated with the sunscreen. The system is calibrated against a series of sunscreens of known SPF (4 through 36) determined in-vivo using the FDA monograph method (Federal Register, Aug. 25, 1978, Sunscreen drug products for over-the-counter human drugs. pp 38206-38269.) The resulting SPF of the composition of Example I above when measured in-vitro was 31.5 and the composition was aesthetically satisfactory and stable.

EXAMPLE II 139 ml of deionized water was added to the receptacle. 0.91 g of Carrageenan was added to the receptacle. The composition was mixed until free from lumps. The mixture was heated to 80° C. 13.59 grams of vegetable glycerin was then added to the receptacle. The ingredients in the receptacle were then mixed until completely uniform. In a second receptacle, 22.6 g of rice bran oil, 27.18 g of phosphatidyl choline, 36.24 g of carrier oils, 9.06 g of stearic acid, 0.46 g of orange wax, 11.3 g of beeswax, and 0.91 g of vitamin e oil (tocopherol) were mixed until all solids were dissolved, and the mixture was heated to 75° C. 54.41 grams of micronized zinc oxide (Z-Cote®) was sprinkled in slowly and homogenized until smooth and uniform. 21.85 grams of micronized titanium dioxide was sprinkled in slowly and homogenized until smooth and uniform. The temperature of this receptacle was increased to 80° C. The first receptacle was then added to the second with vigorous mixing at 80° C. Mixing continued for 30 minutes until the composite was smooth and homogenous. The temperature of the receptacle was lowered to 45° C. 1.13 grams of Grapefruit Seed Extract (GSE) was added, while mixing thoroughly. 0.453 grams of ascorbyl palmitate was added, while mixing thoroughly. 0.226 grams of Biovert® substrate, a product of Arch Chemicals and a composite of glucose, lactoperoxidase, and glucose oxidase was then added, mixing thoroughly. 0.5 grams of orange oil was added. The receptacle was mixed until smooth and homogenous.

The resulting SPF of the composition of Example II above when measured in vitro was 30.7 and the composition was aesthetically satisfactory and stable.

EXAMPLE III 139 ml of deionized water was added to the receptacle. 0.91 g of Carrageenan was added to the receptacle. The composition was mixed until free from lumps. The mixture was heated to 80° C. 13.59 grams of vegetable glycerin and 68.0 grams of Aloe Vera gel were then added to the receptacle. The ingredients in the receptacle were then mixed until completely uniform. In a second receptacle, 22.6 g of rice bran oil, 27.18 g of phosphatidyl choline, 36.24 g of carrier oils, 9.06 g of stearic acid, 0.46 g of orange wax, 11.3 g of beeswax, and 0.91 g of vitamin E oil (tocopherol) were mixed until all solids were dissolved, and the mixture was heated to 75° C. 54.41 grams of micronized zinc oxide (Z-Cote®) was sprinkled in slowly and homogenized until smooth and uniform. 21.85 grams of micronized titanium dioxide was sprinkled in slowly and homogenized until smooth and uniform. The temperature of this receptacle was increased to 80° C. The first receptacle was then added to the second with vigorous mixing at 80° C. Mixing continued for 30 minutes until the composite was smooth and homogenous. The temperature of the receptacle was lowered to 45° C. 22.67 grams of Aloe Vera gel was added, while mixing thoroughly. 1.13 grams of Grapefruit Seed Extract (GSE) was added, while mixing thoroughly. 0.453 grams of ascorbyl palmitate was added, while mixing thoroughly. 0.226 grams of Biovert® substrate, a product of Arch Chemicals and a composite of glucose, lactoperoxidase, and glucose oxidase was then added, mixing thoroughly. 0.5 grams of orange oil was added. The receptacle was mixed until smooth and homogenous.

The resulting SPF of the composition of Example III was measured in vitro to be 30.9 and the composition was aesthetically satisfactory and stable.

EXAMPLE IV

This example was made in accordance with the method of Example III above, with jojoba oil replacing the rice bran oil in equal quantity by weight. The resulting SPF of the composition of Example IV was tested in vitro to be 30.7 and the composition was aesthetically satisfactory and stable.

EXAMPLE V

This example was made in accordance with the method of Example IV above, without the addition of micronized titanium dioxide in the composition. The resulting SPF of the composition of Example V was tested in vitro to be 19.6 and the composition was aesthetically satisfactory and stable.

EXAMPLE VI

This example was made in accordance with the method of Example I above, with twice as much aloe vera gel (a total of 12 g) used in each instance of its addition into the composition. The resulting SPF of the composition of Example VI is in the range of 31.5-33 when measured in vitro and the composition is aesthetically satisfactory.

EXAMPLE VII

This example was made in accordance with the method of Example I above, with three times as much aloe vera gel (a total of 18 g) used in each instance of its addition into the composition. The resulting SPF of the composition of Example VII is in the range of 31.5-35 when measured in vitro and the composition is aesthetically satisfactory.

EXAMPLE VIII

This example was made in accordance with the method of Example I above, with four times as much aloe vera gel (a total of 24 g) used in each instance of its addition into the composition. The resulting SPF of the composition of Example VIII is in the range of 31.5-37 when measured in vitro and the composition is aesthetically satisfactory.

EXAMPLE IX 26.30 ml of deionized water was added to a receptacle. 20.0 grams of Cold Pressed Aloe, 1.75 grams of vegetable glycerin, and 0.25 grams of grapefruit seed extract were mixed into the water. 0.35 g of Xanthan gum was added to the receptacle, with good mixing, until all ingredients were dissolved. The mixture was heated to 40° C. In a second receptacle, 19.2 g of rice bran oil mixed together with 3.5 g of dispersed phosphatidyl choline, 7.0 g of suitable carrier such as castor oil, avocado oil, broccoli seed oil, keratin, micronized or colloidal bentonite, etc. (essential oils or equivalent SPF boosting agents can be used), 0.1 g of orange wax, and 2.5 g of beeswax were mixed until all solids were dissolved, and the mixture was heated to 65° C. When the solution of the second receptacle was heated and became homogenous, 12.0 grams of micronized zinc oxide (Z-Cote®), 4.8 grams of natural source tocopherol (D-alpha), and 4.8 grams of T-Cbte® are added to this second receptacle requiring good agitation and maintaining temperature until the micronized powders were properly wetted. A high-energy mixer was used to disperse the ingredients. The first receptacle (water phase) was then added to the second receptacle (oil phase) with high-speed mixing. On a small scale (less than 200 grams), the addition of phases can be reversed. Mixing continued until the composite was cooled. To this mixture, 1.0 gram of Biovert® substrate (a product of Arch Chemicals and a composite of glucose, lactoperoxidase, and glucose oxidase) was then added, mixing thoroughly. 0.05 grams of Biovert® enzyme was added. The receptacle was mixed until smooth and homogenous.

The resulting SPF of the composition of Example IX above when measured in vitro was 30.9 and the composition was aesthetically satisfactory and stable.

EXAMPLES X-XVIII

Beeswax was heated until melted. The following ingredients were then added, in decreasing order of weight: coconut oil, sunflower oil, tocopherol acetate, tocopherol, lanolin, peppermint oil, comfrey root extract, and rosemary extract. No component was added in greater quantity than the initial beeswax. The composition was stirred for several minutes while a constant temperature was maintained above the melting point for beeswax (146 F/62 C). This composition was then mixed thoroughly with each of the above compositions described in Examples I-IX, at a 90-10 ratio, and then poured into a receptacle and cooled.

| Example # | Current Composition mixed at 90-10 ratio with: |
|---|---|
| X | Example 1 |
| XI | Example 2 |
| XII | Example 3 |
| XIII | Example 4 |
| XIV | Example 5 |
| XV | Example 6 |
| XVI | Example 7 |

-continued

| Example # | Current Composition mixed at 90-10 ratio with: |
|---|---|
| XVII | Example 8 |
| XVIII | Example 9 |

EXAMPLES XIX-XXVII

Beeswax was heated until melted. The following ingredients were then added, in decreasing order of weight: coconut oil, sweet almond oil, tocopherol acetate, tocopherol, lanolin, peppermint oil, comfrey root extract, and rosemary extract. Coconut oil was added in greater quantity than the beeswax, all other ingredients in lower quantity. The composition was stirred for several minutes while a constant temperature was maintained above the melting point for beeswax (146 F/62 C). This composition was then mixed thoroughly with the above compositions described in Examples I-IX at a 90-10 ratio, and then poured into a receptacle and cooled.

| Example # | Current Composition mixed at a 90-10 ratio with |
|---|---|
| XIX | Example 1 |
| XX | Example 2 |
| XXI | Example 3 |
| XXII | Example 4 |
| XXIII | Example 5 |
| XXIV | Example 6 |
| XXV | Example 7 |
| XXVI | Example 8 |
| XXVII | Example 9 |

EXAMPLES XXVIII-XXXVI

An oil phase was prepared by combining sunflower oil, stearic acid, coconut oil, beeswax, tocopherol acetate, orange wax, and beta carotene and stirring the resulting mixture under heat at 80 C until homogeneous. To the oil phase was added sucrose stearate and the resulting mixture was heated, at about 50 C. In a separate container a water phase was prepared by dissolving vegetable glycerin and xanthan gum into deionized water. The water and oil phases were combined. Sodium Borate, Biovert® substrate, and aloe vera gel were added and stirred until homogenous. To the resulting mixture was added fragrance at room temperature and the mixture was allowed to equilibrate overnight. This composition was then mixed thoroughly, at a 90-10 ratio, with the above compositions described in Examples I-IX, and then poured into a receptacle and cooled.

| Example # | Composition + |
|---|---|
| XXVIII | Example 1 |
| XXIX | Example 2 |
| XXX | Example 3 |
| XXXI | Example 4 |
| XXXII | Example 5 |
| XXXIII | Example 6 |
| XXXIV | Example 7 |
| XXXV | Example 8 |
| XXXVI | Example 9 |

EXAMPLE XXXVII 423.58 ml of deionized water was added to the receptacle. The water was heated to 80° C. 15.0 grams of vegetable glycerin was then added to the receptacle, along with 30.0 g of Aloe Vera Gel. The receptacle was then mixed until completely uniform. In a second receptacle, 15.0 g of sunflower oil, 30.0 g phosphatidyl choline, 1.0 g of coconut oil, 80.0 g of carrier oils, 10.0 g of stearic acid, 0.0005 g of beta carotene, 1.0 g of orange wax, 1.0 to 5.0 g of beeswax, and 0.5 g of vitamin e oil (tocopherol) were mixed until all solids were dissolved, and the mixture was heated to 75° C. Optionally 5.0 g Crodesta F-160® (produced by Croda USA) was slowly added, while maintaining the temperature at 75° C. 80.0 grams of micronized zinc oxide (Z-Cote®) was sprinkled in slowly and homogenized until smooth and uniform. 10.0 grams of Sensient Cosmetic Microspheres CM-111® was sprinkled in slowly and homogenized until smooth and uniform. The temperature of this receptacle was increased to 80° C. The first receptacle was then added to the second with vigorous mixing at 80° C. Mixing continued for 30 minutes until the composite was smooth and homogenous. The temperature of the receptacle was lowered to 45° C. 10.0 grams Aloe Vera gel was added, while mixing thoroughly. 0.2 g of borax granular was added, while mixing thoroughly. 5.0 grams of Grapefruit Seed Extract (GSE) was added, while mixing thoroughly. 0.5 grams of ascorbyl palmitate was added, while mixing thoroughly. 0.5 grams of milk powder and 0.5 grams of buttermilk powder were added, while mixing thoroughly. 5.25 grams of Biovert® substrate, a product of Arch Chemicals and a composite of glucose, lactoperoxidase, and glucose oxidase was then added, mixing thoroughly. 1.0 grams of rosemary oil, 0.5 g of peru balsam oil, and 1 gram of olibanum oil (frankincense) were then added. The receptacle was mixed until smooth and homogenous. The composition was cooled and poured into a container allowing for a spray application product.

The invention claimed is:
1. A non-toxic, non-endocrine disrupting composition comprising:
 a) 2 wt. % to 25 wt. % of a mixture of cosmetic microspheres and at least one micronized inorganic sun-block or sunscreen agent selected from the group consisting of micronized titanium dioxide and micronized zinc oxide;
 b) an emollient mixture comprising aloe vera and vegetable glycerine;
 c) at least one emulsifier wherein said emulsifier includes phosphatidylcholine;
 d) 0.1 wt. % to 10 wt. % of a carrier oil component;
 e) an SPF boosting agent that is neither toxic nor endocrine disrupting selected from the group consisting of:
 (e1) mixture of the following ingredients in decreasing order of weight percentage, beeswax, coconut oil, sunflower oil, tocopherol acetate, tocopherol, lanolin, peppermint oil, comfrey root extract, and rosemary extract; and
 (e2) mixture of the following ingredients in decreasing order of weight percentage, beeswax, coconut oil, sweet almond oil, tocopherol acetate, tocopherol, lanolin, peppermint oil, comfrey root extract, and rosemary extract; and
 f) water;
 wherein (b) emollient mixture together with (d) carrier oil component comprise from 2 wt. % to 40 wt. % of the composition, and the ratio of the micronized inorganic sun-block or sunscreen agent to the weight of the carrier oil component and the emollient mixture combined is between 0.25:1 and 2:3;

wherein the pH of the non-toxic, non-endocrine disrupting composition is from about 6.5 to 8.5;

wherein the composition indicates a non-detect for estrogenic activity at less than 0.308 pg/g 17β-estradiol equivalent when tested by an HTPS method for estrogen active compounds; and wherein said composition provides a Sun Protection Factor (SPF) of at least 15.

2. The non-toxic, non-endocrine disrupting composition of claim 1 wherein said carrier oil component comprises one or more silicone oils.

3. The non-toxic, non-endocrine disrupting composition of claim 1, wherein said micronized inorganic sunblock or sunscreen agent is between 4.5 wt. % and 18 wt. % of said composition.

4. The non-toxic, non-endocrine disrupting composition of claim 1 wherein the composition has an SPF value of at least 30.

5. The non-toxic, non-endocrine disrupting composition of claim 1 wherein the composition has an SPF value of at least 45.

6. The non-toxic, non-endocrine disrupting composition of claim 1, wherein the said composition further comprises one or more of stearic acid, sodium borate, xanthan gum, sucrose stearate, glucose, glucose oxidase, lactoperoxidase, beta-carotene or fragrance.

7. The non-toxic, non-endocrine disrupting composition of claim 6 wherein the composition has an SPF value of at least 30.

8. The non-toxic, non-endocrine disrupting composition of claim 6 wherein the composition has an SPF value of at least 45.

9. The non-toxic, non-endocrine disrupting composition of claim 1 wherein the phosphatidylcholine is dissolved in an oil.

* * * * *